(12) United States Patent
Briand et al.

(10) Patent No.: US 7,199,215 B1
(45) Date of Patent: Apr. 3, 2007

(54) PSEUDOPEPTIDE, SYNTHESIS METHOD, REAGENT AND APPLICATIONS

(75) Inventors: Jean-Paul Briand, Strasbourg (FR); Vincent Semetey, Strasbourg (FR); David Limal, Schiltigheim (FR)

(73) Assignee: Biomerieux, Marcy l'Etoile (FR)

( * ) Notice: Subject to any disclaimer, the term of this patent is extended or adjusted under 35 U.S.C. 154(b) by 0 days.

(21) Appl. No.: 09/889,178

(22) PCT Filed: Jan. 12, 2000

(86) PCT No.: PCT/FR00/00053

§ 371 (c)(1), (2), (4) Date: Jan. 15, 2002

(87) PCT Pub. No.: WO00/42065

PCT Pub. Date: Jul. 20, 2001

(30) Foreign Application Priority Data

Jan. 15, 1999 (FR) .................................. 99 00597

(51) Int. Cl.
*A61K 38/00* (2006.01)
(52) U.S. Cl. .................................................... 530/300
(58) Field of Classification Search ................ 530/300
See application file for complete search history.

(56) References Cited

FOREIGN PATENT DOCUMENTS

| EP | 0 126 974 A1 | 12/1984 |
|----|--------------|---------|
| WO | WO 92/13883 | 8/1992 |
| WO | WO 97/18475 | 5/1997 |

OTHER PUBLICATIONS

Rudikoff et al. Single amino acid substitution altering antigen-binding specificity. Proc Natl Acad Sci U S A. Mar. 1982;79(6):1979-83.*

Limal et al. Direct synthesis of N-protected B-amino dimethylhydroxamates: application to the solid-phase synthesis of a peptide incorporating a new amide bond surrogate omega (CH2Ch2NH). Tetrahedron Letters 39 (1998) 4239-4242.*

Bradshaw et al., "Synthesis and characterization of Selective Fluorescent Ligands for the Neurokinin NK$_2$Receptor", J. Med. Chem., vol. 37, 1994, pp. 1991-1995, XP002117380.

Dallaire et al., "Synthesis of New Building Blocks: Towards the Analogs of Peptide Nucleic Acids (PNAs)$^{is}$", Tetrahedron Letters, vol. 39, No. 29, Jul. 16, 1998, pp. 5129-5132, XP004162398.

Limal et al., "Solid-phase Synthesis of N, N'—Unsymmetrically Substituted Ureas: Application to the Synthesis of Carbaza Peptides", Tetrahedron Letters, vol. 40, No. 14, Apr. 2, 1999, pp. 2749-2752 XP004159428.

Nouvet et al., "Synthesis of New Perhydro-(1,4)-diazepin-2-ones as Constrained Peptidominates", Tetrahedron Letters, vol. 39, No. 15, Apr. 9, 1998, p. 2099-2102, XP004110641.

Ostankovitch et al., "A Partially Modified Retro-Inverso Pseudopeptide Modulates the Cytokine Profile of CTL Specific or Influenza Virus Epitope", Journal of Immunology, 1998, pp. 200-208.

Briand et al., "A retro-inverso peptide corresponding to the GH loop of foot-and-mouth disease virus elicits high levels of long-lasting protective neutralizing antibodies", Proc. Natl. Acad. Sci, USA, vol. 94, pp. 12545-12550, Nov. 1997.

Atwood et al., "Peptide Based Inhibitors of Interleukin-8: Structural Simplification and Enhanced Potency", Bioorganic & Medicinal Chemistry Letters, vol. 7, No. 4, pp. 429-432, 1997.

Hermanson, "Bioconjugate Techniques", Academic Press, San Diego, 1996.

Stemmer et al., "Protection against Lymphocytic Choriomeningitis Virus Infection Induced by a Reduced Peptide Bond Analogue of the H-$2D^b$-restricted $CD8^+$T Cell Epitope GP33", The Journal of Biological Chemistry, vol. 274, No. 9, Feb. 26, 1999, pp. 5550-5556.

Fehrentz et al., An Efficient Synthesis of Optically Active a-(t-Butoxycarbonylamino)-aldehydes from a-Amino Acids, Synthesis, 1983, pp. 676-678.

Lloyd-Williams et al., "Chemical Approaches to the Synthesis of Peptides and Proteins", CRC press, Boca Raton, 1997.

Osmanov, "Report of a WHO workshop on synthetic peptides in HIV diagnosis and AIDS-related research, Moscow May 24-26 1989", AIDS 1991, 5:WHO1-WHO9.

Fujii et al., "Trimethysilyl Trifluoromethanesulphonate as a Udeful Deprotecting Reagent in Both Solution and Solid Phase Peptide Syntheses", J. Chem. Soc., Chem. Commun., 1987, pp. 274-275.

Gante, Synthesis, pp. 405-413, 1989.

Rammense, "chemistry of peptides associated with MHC class I and class II molecules", Current Opinion in immunology 1995, 7:85-96, Current Biology LTD.

Han et al., "Journal of the American Chemical Society", vol. 118, No. 11, Mar. 20, 1996.

Hutchins et al., "A Strategy for Urea Linked Diamine Libraries", Tetrahedron Letters, vol. 36, No. 15, pp. 2583-2586, 1995.

Camarero et al., "Chemical ligation of unprotected peptides from a solid support", Journal of Peptide Research, vol. 51, 1998, pp. 303-316.

King et al., "A cleavage method which minimizes side reactions following Fmoc solid phase peptide synthesis", Journal of Peptide Protein Research, vol. 36, 1990, pp. 255-266.

(Continued)

*Primary Examiner*—Bruce R. Campbell
*Assistant Examiner*—Maury Audet
(74) *Attorney, Agent, or Firm*—Oliff & Berridge, PLC

(57) ABSTRACT

The invention concerns a pseudopeptide of at least 6 amino acids comprising at least a unit selected among the general formulae (I) and/or (II) wherein: $R_1$, $R_2$ and $R_3$ each independently of one another represent a side-chain of amino acids and can be identical or different; X represents an oxygen or sulphur atom. The invention also concerns its synthesis process, a reagent containing it, a detection kit comprising such a reagent, a method for detecting an antigen or an antibody using said pseudopeptide, and antibody or and anti-idiotype and finally a therapeutic composition.

14 Claims, 2 Drawing Sheets

OTHER PUBLICATIONS

Limal et al., "Solid-phase synthesis and on-resin cyclization of a disulfide bond peptide and lactam analogues corresponding to the major antigenic site of HIV gp41 protein", Journal of Peptide Research, vol. 52, 1998, pp. 121-129.

Limal et al., Direct synthesis of N-protected B-amino dimethylhydroxamates: Application to the solid-phase synthesis of a peptide incorporating a new amide bond surrogate [$CH_2CH_2NH$], Tetrahedron Letters, vol. 39, 1998, pp. 4239-4242.

Regenmortel, "Transcending the Structuralist Paradigm in Immunology—Affinity and Biological Activity Rather Than Purely Structural Considerations Should Guide the Design of Synthetic Peptide Epitopes", Proteins & Nucleic Acids, vol. 1, 1995, pp. 109-116.

Regenmortel, "Structural and Functional Approaches to the Study of Protein Antigenicity", Immunology Today, vol. 10, No. 8, 1989, pp. 266-271.

Majer et al., "A Safe and Efficient Method for Preparation of N,N'-Unsymmetrically Distributed Ureas Utilizing Triphosegen", J. Org. Chem., 1994, vol. 59, pp. 1937-1938.

Mendre et al., Pharmacological activity of cholccystokin analogues modified in the Met[28]-Gly[29] region, European Journal of Pharmacology, vol. 186, 1990, pp. 213-222.

Aichele et al., "T Cell Priming Versus T Cell Tolernace Induced by Synthetic Prptides", J. Exp. Med. vol. 182, Jul. 1995, pp. 261-266.

Perrin et al., "Purification of Laboratory Chemicals", 2nd edition, Pergamon Press, Oxford.

Quibell et al., "Synthesis of Azapeptides by the Fmoc/tert-Butyl/Polyamide Technique", J. Chem. Soc., Perkin Trans., I 1993.

Calbo et al., "Role of Peptide Backbone in T Cell Recognition", Journal of Immunology, 1999, 162: 4657.

Tourdot et al., "Chimeric Peptides: A New Approach to Enhancing the Immunogenicity of Peptides with Low MHC Class 1 Affinity: Application in Antiviral Vaccination", Journal of Immunology, 1997, 159: 2391.

Grant, "Synthetic Peptides", WH Freeman and Company, New York, 1992.

Greene et al., "Protective Groups in Organic Synthesis", second edition, John Wiley & Sons, New York 1991.

Bodanszky et al., "The Practice of Peptide Synthesis", Springer Verlag, Berlin, 1984.

Lu et al., "Total chemical synthesis of bovine pancreatic trypsin inhibitor by native ligation", FEBS Letters, 429, pp. 31-35, 1998.

Wong, "Chemistry of Protein Conjugation and Cross-Linking", CRC Press, Boca Raton, 1991.

Zhang et al., ∂Formation of Urea Dipeptides from Carbonyldiimidazole: Application toward the Protease Inhibitors GE 20372 and MAPI, J. Org. Chem., 1997, vol. 62, pp. 6420-6423.

Takeda et al., Convenient Methods for Syntheses of Active Carbanates, Ureas, and Nitrosoureas Using N, N[1]-disuccinimido Carbonate (DSC)[1], Tetrahedron Letters, vol. 24, No. 42, pp. 4569-4572, 1983.

* cited by examiner

PSEUDOPEPTIDE, SYNTHESIS METHOD, REAGENT AND APPLICATIONS

For many years, many teams have focused on synthesizing analogs of peptides or proteins which mimic the biological activities of natural peptides or proteins. There may be mentioned, by way of example, the peptide analogs obtained by replacing one or more amino acids of the L series with one or more corresponding amino acids of the D series, the peptides exhibiting a modification at the level of at least one of the peptide bonds, such as the retro, inverso, retro-inverso, carba and aza bonds.

The carba bond ($CH_2$—$CH_2$) has been described as a potential mimic of the peptide bond (Mendre C. et al., European J. Pharmacol., 186, p. 213–222, 1990; Attwood et al., Bioorg. Med. Chem. Lett., 7, p. 429–432, 1997). Moreover, the partial or complete replacement of the α-carbon by a nitrogen atom on a peptide has made it possible to obtain advantageous pseudopeptides called azapeptides and azatides respectively (Gante, J., Synthesis, p. 405–413, 1989; Han H. and Janda K. D., J. Amer. Chem. Soc, 118, p. 2539–2544, 1996).

In general, these peptide analogs, called pseudopeptides, have, as a first advantage, a metabolic stability which is greater than that of natural peptides or proteins because they are not degraded by natural proteases or are degraded less rapidly. Moreover, the conformational changes induced by these chemical modifications can improve the biological properties of these pseudopeptides, see for example the decapeptide analogs which are antagonists of the hypothalmic hormones and which are described in WO-A-92/13883.

While the techniques for the synthesis of so-called natural peptides, in particular on solid supports, are well established and make it possible to easily prepare peptides comprising several tens of amino acids, the introduction of these modifications in order to prepare pseudopeptides renders the synthesis more complex, in particular for long pesudopeptides.

Moreover, in the field of immunology and both in the diagnosis of viral or autoimmune diseases and in immunotherapy or vaccination, the synthetic peptides mimicking the epitopes of proteins represent a valuable alternative. The size of the peptides which are analogs of these antigenic derminants or epitopes is an important factor in the choice of these peptides and has been the subject of numerous publications (M.H.V. Regenmortel, Immunology Today, 10(8), p. 266–271, 1989 or M.H.V. Regenmortel, Biomedical Peptides, Proteins & Nucleic Acids, 1, p. 109–116, 1995). While originally it was accepted that an epitope comprises between 15 and 22 amino acids, recent studies show that this size may be reduced to a few amino acids. In the immunity domain, crystallographic studies on the interaction of peptides and the major histocompatibility complex (MHC) indicate a size of 9 to 13 amino acids for a good interaction with the MHC class I molecules and 9 to 25 for the MHC class II (H.. G. Rammensec, Current Opinion in Biotechnology, 7, p. 86–96, 1995). Likewise, in diagnosis, the size is a critical factor for the use of peptides. In the case of HIV (human immunodeficiency virus), the smallest epitopes comprising from 4 to 6 amino acids but the peptides used still have a size greater than at least 12 amino acids eater than at least 12 amino acids (D. Osmanov, AIDS, 5(1), WHO1–WHO9, 1991). In another example, such as the diagnosis of Chagas' disease, the peptides used comprise a minimum of 12 amino acids (WO-A-97/18475). In (Bradshaw C. G. et col., J. Med. Chem., 37, 1991–1995, 1994) fluorescent probes which are analogs of the heptapeptide antagonist of $NK_2$ were obtained by substitution of an amino acid and coupling with a fluorophore.

It is the object of the present invention to describe a novel family of pseudopeptides comprising a novel carbaza unit significantly modifying the peptide backbone and whose use in the context of peptide synthesis is easy both in solid phase and in liquid phase, and this even for peptides of a large size and in particular greater than 6 amino acids. This novel family of pseudopeptides can be used in the diagnostic field to provide in vitro methods for the diagnosis of pathology conditions associated with the presence of endogenous or exogenous proteins in an individual, or in the therapeutic field, and in particular immunotherapy or vaccination. These pseudopeptides have a size of at least 6 amino acids comprising at least one unit chosen from the B units of general formula I and/or II defined below:

in which:

$R_1$, $R_2$ and $R_3$ each independently of one another represent an amino acids side chain and may be identical or different, and X represents an oxygen or sulfur atom, preferably an oxygen atom, Advantageously, $R_2$ represents a hydrogen atom.

The expresssion amino acids is understood to mean the primary amino acids which encode proteins, the amino acids derived after enzymatic action such as trans-4-hydroxyproline and the natural amino acids but which are not present in proteins, such as norvaline, N-methyl-L-leucine, staline (Hunt S, in Chemistry and Biochemistry of the amino acids, Barett G. C., ed., Chapman and Hall, London, 1985), the amino acids protected by chemical functional groups which can be used in synthesis on solid supports or in liquid phase and the non-natural amino acids. Examples of these non-natural amino acids are given in the Novabiochem catalog (Catalog & Peptide synthesis Handbook; 199; CH-4448, Läufelfinfgen, Switzerland) or the Néosystem catalog (Catalog 1997/1998; 67100 Strasbourg, France). and the non-natural amino acids. Examples of these non-natural amino acids are given in the Novabiochem catalog (Catalog & Peptide synthesis Handbook; 1999; CH-4448, Läufelfinfgen, Switzerland) or the Néosystem catalog (Catalog 1997/1998; 67100 Strasbourg, France).

The expression amino acids side chain is understood to mean all the side chains of the amino acids as defined above. In the case of proline, it is understood that the side chain $R_1$ or $R_2$ in the formula of the B unit cyclizes so as to bond to the nitrogen in the alpha position. Likewise, $R_1$ and $R_2$ may bind covalently.

Preferably, the pseudopeptide comprises at least 9 amino acids. Advantageously, in the case of diagnosis, the pseudopeptide comprises at least 12 amino acids. The B unit as defined represents 2 amino acids since the linear backbone of said B unit possesses a structure with 6 atoms.

Preferably, the NH functional group of formula I and the $NR_3$ functional group of formula II are linked to a group CX, and/or the CX functional group of formulae I and II are linked to a group NH or $NR_3$, said groups CX, NH and $NR_3$ belonging to a peptide or pseudopeptide unit.

The invention also relates to a method for synthesizing the pseudopeptide containing at least one B unit. For that, the molecule(s) required are monoprotected diamines having the following structure IIIa or IIIb:

where

GP represents any group for protecting the amine functional group, such as for example those described in T. W. Greene and P. G. M. Wuts, Protective Groups in Organic Synthesis, 2nd edition, John Wiley and Sons, New York, 1991; preferably those commonly used in peptide synthesis, namely:

Boc (tert-butyloxycarbonyl),
Fmoc (9-fluorenylmethyleneoxycarbonyl),
Cbz (carboxybenzyl), or
Alloc (allyloxycarbonyl), and $R_1$, $R_2$ and $R_3$ each independently of one another represent an amino acids side chain and may be identical or different.

This molecule is then coupled to an amine via a carbonylating agent. By way of example, there may be mentioned N,N'-carbonyldiimidazole (CDI) (Zhang, X.; Rodrigues, J.; Evans, L.; Hinckle, B.; Ballantyne, L.; Pena, M. J. Org. Chem. 62, 6420–6423, 1997), p-nitrophenyl carbamate (Hutchins, S. M. & Chapman K. T. Tet Lett. 36, 2583–2586, 1995), 2,4-dinitrophenyl carbonate (Quibell, M.; Turnell, W. G.; Johnson, T. J. Chem. Soc. Perkin Trans. 12843–2849), N,N'-disuccunimidyl carbonate (DSC) (Takeda, K.; Akagi, Y.; Saiki, A.; Tsukahara, T.; Ogura, H. Tet. Lett. 1983, 24, 4569–4572) and more particularly triphosgene (Majer, P. & Randad, R. S. J. Org. Chem. 59, 1937–1938, 1994). This reaction may be carried out on a solid support or in homogeneous phase.

Using this coupling technique, the B unit may be introduced at any position of the pseudopeptide and it is easy to prepare a pseudopeptide comprising several B units corresponding to the formulae I and/or II. The pseudopeptide may comprise exclusively a succession of B units corresponding to the formulae I and/or II.

The pseudopeptide according to the invention may be modified after or during the synthesis, for example by coupling with tracers, ligands or anti-ligands, proteins, vitamins, by phosphorylation, sulfation, glycosylation or hydroxylation. The pairs biotin/streptavidin, lectin/sugar, hapten/antibody, chelator/chelated molecules, hormone/receptor, polynucleotide/complementary polynucleotide are examples of ligand/anti-ligand pairs.

An example of a strategy for modifying a peptide with biotin is given in Limal, D.; Briand, J. P.; Dalbon, P.; Jolivet, M., 1998, J. Peptide Res. 52, 121–129.

The structure of the pseudopeptide may undergo modifications such as intrapeptide or interpeptide bonds. As examples for the formation of an intrapeptide bond, the creation of disulfide bridges between various cysteine side chains or the formation of lactams between two side chains or between the two C-terminal and N-terminal ends may be envisaged. The interpeptide bonds may lead to the formation of peptide multimers crosslinked or otherwise by the use of bifunctional coupling reagents.

Examples of a coupling strategy for the modification of the pseudopeptide are given in Chemistry of protein conjugation and cross-linking, Wong S. S., CRC Press, Boca Raton, 1991 or in Bioconjugate techniques, Hermanson G. T., Academic Press, San Diego, 1996. The pseudopeptides according to the invention may be linear cyclic or branched.

The synthesis of the pseudopeptide may be carried out on a solid support by conventional recurring techniques, by chemical ligation techniques (W. Lu et al., FEBS Letters, 429, p. 31–35, 1998 or J. A. Camarero et al., J. Peptide Res., 51, p. 303–316, 1998) or by fragment condensing techniques (Chemical approaches to the synthesis of peptides and proteins, Lloyd-Williams P., Albericio F., Giralt E., CRC Press, Boca Raton, 1997) or by combining these various techniques.

Another subject of the invention is a reagent for detecting a pathological condition associated with the presence of endogenous or exogenous proteins, said reagent comprising, in addition, a pseudopeptide of the invention as reactive substance. The pseudopeptide is advantageously labeled with a tracer or biotin. Preferably, the size of the pseudopeptide is at least 12 amino acids.

The pathological conditions may all relate to animal or human pathologies and in particular human pathologies, and in particular pathological conditions of viral or parasitic origin, the field of cancer, autoimmune diseases or neurodegenerative diseases.

The detection of pathological conditions may be carried out in a direct or indirect manner. The term direct is understood to mean the detection of this pathological condition in a biological sample obtained from the human or animal organism such as, for example, blood, urine, sputum or a smear. The term indirect is understood to mean the detection of proteins in samples such as, for example, water, air, food, pharmaceutical products, cosmetics which may come into contact with said human or animal organism to cause a pathological condition.

The subject of the invention is a kit for detecting pathological conditions associated with the presence of endogenous or exogenous proteins comprising the reagent described above, attached to a solid support which is immunologically compatible with said reagent.

The term "solid support" as used here includes all the materials on which a biological molecule may be immobilized for use in diagnostic tests and in separation processes. Natural or synthetic materials, chemically modified or otherwise, may be used as a solid support, in particular polysaccharides such as cellulose-based materials, for example paper, cellulose derivatives such as cellulose acetate and nitrocellulose, dextran; polymers such as polyvinyl chlorides, polyethylenes, polystyrenes, polyacrylates, polyamides or copolymers based on monomers of the styrene type, esters of unsaturated carboxylic acids, vinylidene chloride, dienes or compounds having nitrite functional groups (such as acrylonitrile); copolymers vinyl chloride/ propylene, vinyl chloride/vinyl acetate; natural fibers such as cotton and synthetic fibers such as nylon; inorganic materials such as silica, quartz glass ceramics; latexes, that is to say aqueous colloidal dispersions of any polymer which is insoluble in water; magnetic particles; metallic derivatives, and the like.

The solid support may be in particular in the form of a microtiter plate, a sheet, a cone, a tube, beads, particles and the like.

The attachment of the reagent may be carried out in a direct or indirect manner.

In the direct manner, two approaches are possible: either by adsorption of the reagent onto the solid support, or by covalent bonding. In one variant, the pseudopeptide of the reagent may be coupled to a polypeptide, a protein or a nucleic acid fragment in order to enhance the attachment onto the solid phase.

In the indirect manner, it is possible to attach beforehand (by covalent bonding or adsorption) an anti-reagent capable of interacting with the reagent so as to immobilize the whole onto the solid support. By way of example, streptavidin, adsorbed onto the solid support, can allow the attachment of a pseudopeptide carrying a biotin, or an antibody (monoclonal, polyclonal or an antibody fragment) directed against the B unit of the invention can allow this same attachment of the pseudopeptide.

The invention relates, in addition, to a method for detecting and/or assaying biological molecules, and in particular antibodies, present in a sample in which the reagent according to the invention is used to form an immune complex with said biological molecules if they are present in the sample.

The invention relates in particular to a method for detecting and/or assaying antibodies in a sample, comprising the steps consisting in bringing said sample into contact with a reagent of the invention under conditions allowing an immunological reaction, and then in detecting and/or assaying the immune complex which may be formed.

In a particular mode, the reagent of the invention is attached to the solid phase and the immune complex is detected with the aid of a second antibody labeled with a tracer.

In another particular mode, the immune complex between the labeled reagent and the biological molecule is formed in the homogeneous phase and its presence is detected by a physicochemical modification of the tracer linked to the formation of the immune complex.

By way of example, this second antibody is a monoclonal or polyclonal antibody or an Fab-type fragment, directed for example against human antibodies in the case of a human biological sample.

The term tracer is intended to mean an entity capable of generating a detectable signal.

The tracer may be chosen in particular from:

enzymes which produce a signal which can be detected for example by colorimetry, fluorescence, luminescence, such as horseradish peroxidase, alkaline phosphatase, β-galactosidase, glucose-6-phosphate dehydrogenase, chromophores such as fluorescent compounds, luminescent compounds or colorants, groups with an electron density which can be detected by electron microscopy or by their electrical properties such as conductivity, amperometry, voltametry, impedance measurements, groups which can be detected by optical methods such as diffraction, surface plasmon resonance, contact angle variation or physical methods such as atomic force spectroscopy or tunnel effect.

The labeling with a tracer may be carried out either in a direct or indirect manner.

The expression direct labeling is understood to mean the covalent attachment of the tracer. The expression indirect labeling is understood to mean the noncovalent attachment of the tracer, in particular by ligand/anti-ligand interactions.

The invention also relates to a method for detecting and/or assaying an antigen present in a sample by a competition technique in which said sample is brought into contact, simultaneously or in two stages, with a predetermined quantity of an antibody directed against a portion of the antigen and a predetermined quantity of a reagent of the invention, and the presence and/or the quantity of antigen present in said sample is determined.

In a particular mode, it is the antibody which is attached to the solid phase and the reagent of the invention is labeled with a tracer.

The invention also relates to a method for detecting and/or assaying an antibody present in a sample by a competition technique in which said sample is brought into contact simultaneously with a predetermined quantity of an antigen at least a portion of which is recognized by said antibody and a predetermined quantity of a reagent of the invention, and the presence and/or the quantity of antibody present in said sample is determined.

In a particular embodiment, the antigen is attached to the solid phase and the reagent of the invention is labeled with a tracer. In another variant, the reagent is attached to the solid phase and the antigen is labeled with a tracer.

The pseudopeptides of the invention are in addition of interest in the production of vaccines. It is now established that peptide analogs have a capacity to stimulate the T lymphocytes (P. Aichele et al., 1995. T cell priming versus T cell tolerance induced by synthetic peptide. J. Exp. Med. 182:261, S. Tourdot et al., 1997. Chimeric peptides: a new approach to enhancing the immunogenicity of peptides with low MHC class I affinity: application in antiviral vaccination. J. Immunol. 159:2391).

Thus, the subject of the invention is also the antibodies directed against the pseudopeptides according to the invention which may be monoclonal or polyclonal. Said antibodies are capable of being obtained by immunizing an animal with at least one pseudopeptide according to the invention. The antibodies according to the invention are more particularly characterized in that they are capable of forming a complex with pseudopeptides and/or the parent proteins or peptides corresponding to the latter.

The expression parent protein is understood to mean a natural protein and the expression parent peptide is understood to mean either a peptide which exists as such in the natural state, in particular in a higher organism, and in particular the human body, or a peptide derived from a protein as it exists in the natural state in the abovementioned organisms, in particular by fragmentation of said protein or by peptide synthesis, or a peptide of immunological interest which is obtained by peptide synthesis, or a peptide derived from a protein as it exists in the natural state but whose immunological activity has been modified, preserved or optimized by replacing certain amino acids, such as for example following a screening of a library of analogous peptides obtained by peptide synthesis.

The anti-pseudopeptide antibodies of the invention recognize the parent peptide or the parent protein with an affinity at least equal to that exhibited by the anti-parent peptide or anti-parent protein antibodies toward the parent peptide or the parent protein. The affinity constant at equilibrium Ka of the complexes is a means of measuring the affinity.

The invention also relates to the anti-idiotypes which can be obtained by immunizing an animal with said antibodies as defined above.

During recent studies, some authors, including those of the present invention (J. P. Briand et al., 1997. A retro-inverso peptide corresponding to the GH loop of foot-and-mouth disease virus elicits high levels of long-lasting protective neutralizing antibodies. Proc. Natl. Sci. USA 94:12545; C. Stemmer et al., 1999. Protection against lymphocytic choriomeningitis virus infection induced by a reduced peptide bond analogue of the H-2 $D^b$-restricted CD8(+) T cel epitope GP33. J. Biol. Chem. 274:5550), have shown that peptide analogs may advantageously replace natural peptides, in therapy. By way of example, it has been observed that the modifications of the peptide backbone can considerably influence the interactions of the MHC complex/peptide with the receptor for the T lymphocytes (C. Stemmer et al., 1999. Protection against lymphocytic choriomeningitis virus infection induced by a reduced peptide bond analogue of the H-2 $D^b$-restricted CD8(+) T cel epitope GP33. J. Biol. Chem. 274:5550; M. Ostankovitch et al., 1998. A partially modified retro-inverso pseudopeptide modulates the cytokine profile of CTL specific for an influenza virus epitope. J. Immunol. 161:200; S. Calbo et al., 1999. Role of peptide backbone in T cel recognition. J. Immunol. 162:4657).

Another application of the pseudopeptides according to the invention is an active therapeutic composition and in particular an active immunotherapeutic composition, preferably a vaccine composition comprising, as active ingredient, a pseudopeptide having a half-life greater than that of the natural proteins or that of the synthetic peptides derived or otherwise from these natural proteins (these natural proteins, or these peptides derived or otherwise from the latter being designated by the expression parent proteins or peptides) of which they are analogs, said active ingredient being optionally in the form of a conjugate or a pharmaceutically acceptable excipient.

The abovementioned pathological conditions which may be treated in the context of the present invention are mainly either diseases of viral, bacterial or parasitic origin, when they are associated with the presence of the microorganism itself, or autoimmune diseases when they are associated with the presence of endogenous proteins or peptides disrupting the normal physiological function of an organism when the latter directly play a role of antibody or induce the formation of antibodies recognizing and altering particular sites of the organism such as, for example, by forming deposits of antibody/antigen complexes or by causing inflammatory states. The abovementioned pathological conditions may also be neurodegenerative diseases when they are associated with the presence, in the organism, of exogenous proteins having the effect of causing neurological lesions. The pseudopeptides used for the preparation of the pharmaceutical compositions or vaccines are advantageously pseudopeptides whose backbone consists solely of a succession of B units of general formula I and/or II.

The invention relates more particularly to the use of a pseudopeptide as defined above, for the preparation of a vaccine in the context of the prevention of pathological conditions associated with the presence, in the body of an individual, of one or more exogenous or endogenous proteins which may be recognized by antibodies directed against the pseudopeptides or directed against the anti-idiotypes according to the invention.

The invention also relates to any pharmaceutical composition comprising at least one pseudopeptide as defined above or at least one abovementioned anti-idiotype, combined with a protein or nonprotein carrier molecule which may induce in vivo the production of antibodies neutralizing said exogenous or endogenous proteins responsible for the pathological condition, or induce in vivo a cytotoxic immune cell response. The invention relates, in addition, to any pharmaceutical composition comprising at least one antibody defined above.

As regards the use of the pseudopeptides in the context of medicaments intended for the treatment of autoimmune diseases, it should be recalled that the pathogenesis of numerous autoimmune diseases involves the presentation of autoantigens (attached to MHC molecules) to the receptor for autoreactive T cells which have somehow escaped the self-tolerance process. Accordingly, the development of novel strategies for modulating the autoreactive T cells response could lead to therapeutic approaches capable of treating certain autoimmune diseases.

Certain autoimmune diseases are associated with specific MHC I or II alleles. Thus, the use of blocking peptides capable of interacting with a given MHC molecule (for example an MHC molecule class II associated with a particular autoimmune disease) but which cannot activate the pathogenic T cell response is promising. However, the degradation of the peptides in the biological media makes their use difficult. In this case, the pseuopeptides, by virtue of their stability, could be very advantageous.

The following examples make it possible to illustrate a few advantages of the invention without, however, limiting the scope thereof. They refer to the accompanying drawing in which.

EXAMPLE 1

Synthesis of a Protected Diamine for the Introduction of the Carbaza Unit B into a Pseudopeptide The route of synthesis used to obtain this amino acid derivative is the following.

Figure 1:
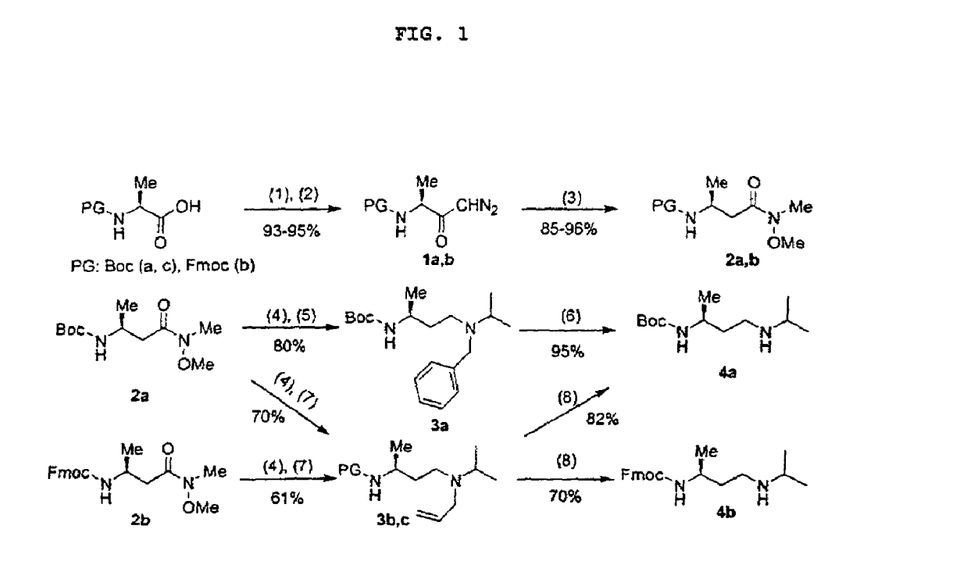
FIG. 1 illustrates the synthesis of a diamine responsible for mimicking the dipeptide sequence (Ala-Val) once introduced into a peptide; this synthesis was carried out according to the two strategies commonly used in peptide synthesis (Boc and Fmoc) to demonstrate the general features of the route proposed.

A natural or non-natural N-protected amino acid is first of all converted by the action of diazomethane in order to obtain the corresponding N-protected diazoketone (1, FIG. 1). The N,O-dimethylhydroxamate of the N-protected β-amino acid 2 is then obtained, by direct Wolff rearrangement in the presence of N,O-dimethylhydroxylamine, according to the method described by Limal et al. (Limal, D.; Quesnel, A.; Briand, J. P. Tet. Lett. 39, 4239–4242, 1998) (2, FIG. 1). This step may be carried out in a more conventional manner, passing via the N-protected β-amino acid. The reduction of this molecule into an aldehyde is carried out by the method described by Fehrentz and Castro (Fehrentz, J. A. & Castro, B. Synthesis 676–678, 1982). A reductive amination between the aldehyde obtained and a protected primary amine leads to the N-protected diamine 3. The protection of the primary amine will be orthogonal to the first protection of the amino acid so as to be able to selectively remove one of the two. By way of example, in the case of an amino acid which is N-protected by a Boc group, the amine to be introduced will be protected by an allyl or benzyl group, while in the case of an amino acid which is N-protected by an Fmoc group, the amine to be introduced will be protected by an allyl group. The deprotection of this group then makes it possible to obtain the monoprotected diamine 4a or 4b.

By way of example, FIG. 1 illustrates the synthesis of a diamine which mimics the dipeptide sequence (Ala-Val) once introduced into a peptide. This synthesis was carried out according to the two strategies commonly used in peptide synthesis (Boc and Fmoc) to demonstrate the general nature of the route proposed. The reaction yields are indicated for each step.

The procedure for this synthesis is described below according to the various steps:

(1) During reaction (1), there are reacted with 1 equivalent of commercial amino acid corresponding to alanine N-protected by the protecting group Boc (Novabiochem, reference 04-12-0002) or the protecting group Fmoc (Novabiochem, reference 04-12-1006), 1.1 equivalents of iBuOCOCl (sold by the company Aldrich, St Quentin Fallavier, France under the reference 17,798–9) and 1.1 equivalents of NMM (4-methylmorpholine, Aldrich, 40770-4), in THF (tetrahydrofuran, Aldrich, 40175-7) at an amino acid concentration of 0.1 molar at the temperature of −25° C. for 1 hour. The intermediate product is filtered in order to remove the salts formed.

(2) This intermediate product then reacts (step (2)) with diazomethane $CH_2N_2$ (prepared from a Diazald precursor sold by the company Aldrich, reference D2,800-0 using the specific setup sold by the company Aldrich under the reference Z10,851-0) in solution in ether, at room temperature, for 2 hours. The solvents are evaporated off with the aid of a rotary evaporator and product 1 is purified by silica chromatography with an ethyl acetate/hexane:30/70 mixture).

(3) Reaction (3) is carried out by mixing 1 equivalent of product 1 with 3 equivalents of $Et_3N$, 0.15 equivalent of $C_6H_5CO_2Ag$ (Aldrich, 22,727-7) in THF (0.1 molar with respect to product 1) and then adding 1.5 equivalents of HN(OMe)Me (obtained by neutralizing with 2 equivalents of $NEt_3$ the acidic precursor sold by Aldrich reference D16,370-8) at a temperature of −25° C. The reaction mixture is brought to room temperature for 2 hours. After concentrating the solvents, washing with a potassium sulfate solution, drying over magnesium sulfate, evaporating the organic solvents and purifying by silica chromatography with an ethyl acetate/hexane:50/50 mixture, product 2 is isolated.

(4) Reaction (4) is carried out by reacting 3 equivalents of $LiAlH_4$ in THF (Aldrich, 21776-6) at a concentration of 0.1 molar with respect to product 2 at the temperature of −30° C. for 1 hour. 50 ml of ethyl acetate are added to the reaction mixture. The excess hydride is then neutralized by adding an aqueous potassium hydrogen sulfate solution, the organic phase is successively washed with a potassium hydrogen carbonate solution and then with a saturated NaCl solution. The organic phase is dried over magnesium sulfate, filtered and evaporated to give the corresponding aldehyde.

(5) Reaction (5) is carried out by reacting 1.1 equivalents of N-isopropylbenzylamine (Aldrich, 13,696-4) and 1.4 equivalents of $NaBH(OAc)_3$ (Aldrich, 31,639-3) in DCE (1,2-dichloroethane, Aldrich, 31992-9) at a concentration of 0.3 molar with respect to product 2a at room temperature for 3 hours. The reaction mixture is treated as indicated in step (4) after evaporation of the DCE.

(6) Reaction (6) is a catalytic hydrogenation carried out in methanol at 0.1 molar with respect to product 3a in the presence of 0.1 equivalent of the reagent palladium on carbon bed (Aldrich, 20,569-9). The reaction mixture is then filtered in order to remove the catalyst and, after evaporating the solvent, product 4a is obtained.

(7) Reaction (7) is carried out by reacting 1.1 equivalents of N-isopropylallylamine and 1.4 equivalents of $NaBH(OAc)_3$ in DCE at a concentration of 0.3 molar with respect to product 2 at room temperature for 3 hours. The treatment carried out to obtain product 3b or 3c is identical to that of step (4).

The synthesis of N-isopropylallylamine is the following.

Allyl bromide (100 mmol, Aldrich, A2,958-5) is slowly added to a stirred solution of isopropylamine (200 mmol, Aldrich 10,906-1), in 40 ml of water, at room temperature. The reaction mixture is then heated under reflux over a period of 4 hours. 10 g of sodium hydroxide (250 mmol) are added to the mixture at 10° C., and the mixture is kept stirred for 1 hour while allowing the temperature to rise to 20° C. The mixture is extracted with ether (twice 30 ml) and then the organic phase is dried over $Na_2SO_4$ and the solvent is evaporated off. The residue is distilled until the expected product is obtained (boiling point 79° C.).

(8) Reaction (8) is carried out by reacting 0.05 equivalent of a mixture $Pd(dba)_2$ (bis(dibenzylideneacetone)palladium (0), sold under the reference 8764 by the company Lancaster, Strasbourg, France) and DPPB (1,4-bis(diphenylphosphino)butane, sold under the reference 8310 by the company Lancaster) in a 1:1 ratio with 2 equivalents of 2-merceptobenzoic acid (Aldrich, T3,320-0) in $CH_2Cl_2$ at a concentration of 0.1 molar with respect to product 3 at room temperature for 2 hours. After evaporation of $CH_2Cl_2$, the reaction mixture is taken up in diethyl ether, and then compound 4b is obtained in the hydrochloride form by precipitation, by bubbling gaseous hydrochloric acid in solution.

The solvents are purified according to the customary methods in organic synthesis (Purification of Laboratory Chemicals, 2nd edition, D. D. Perrin, W. L. F. Armarego, D. R. Perrin, Pergamon Press, Oxford).

The characterization of these intermediates by conventional methods of Nuclear Magnetic Resonance (NMR; Bruker Spectrospin, Bremen, Germany) and mass spectrometry (MS; MALDI TOF, Protein TOF, Bruker Spectroscopin, Bremen, Germany) was carried out and the data are in agreement with the expected theoretical values.

Description of products 4a and 4b:

4a. White solid. $^1H$ NMR (200 MHz, $CDCl_3$) d(ppm) 1.21 (d, 3H, J=6.6 Hz), 1.4–1.44 (m, 6H), 1.42 (s, 9H), 1.77 (m, 1H), 2.30 (m, 1H), 2.88–3.09 (m, 2H), 3.27 (m, 1H), 3.74 (m, 1H), 4.7 (d, 1H) MALDI-TOF MS: m/z 231.2 (M+H$^+$).

4b. White solid (chloride salt). $^1H$ NMR (200 MHz, $CDCl_3$) d(ppm) 1.24 (d, 3H, J=6.1 Hz), 1.39–1.47 (dd, 6H, J=6.5 Hz), 1.65–2.08 (2m, 2H), 2.88–3.08 (2m, 2H), 3.26 (m, 1H), 3.71–3.92 (m, 1H), 4.20 (m, 1H), 4.39 (m, 2H), 5.23 (bb, 1H), 7.27–7.41 (m, 4H), 7.59 (d, 2H, J=6.9 Hz), 7.60 (d, 2H, J=6.8 Hz); MALDI-TOF MS: m/z 353.4 (M+H$^+$).

EXAMPLE 2

Figure 2:
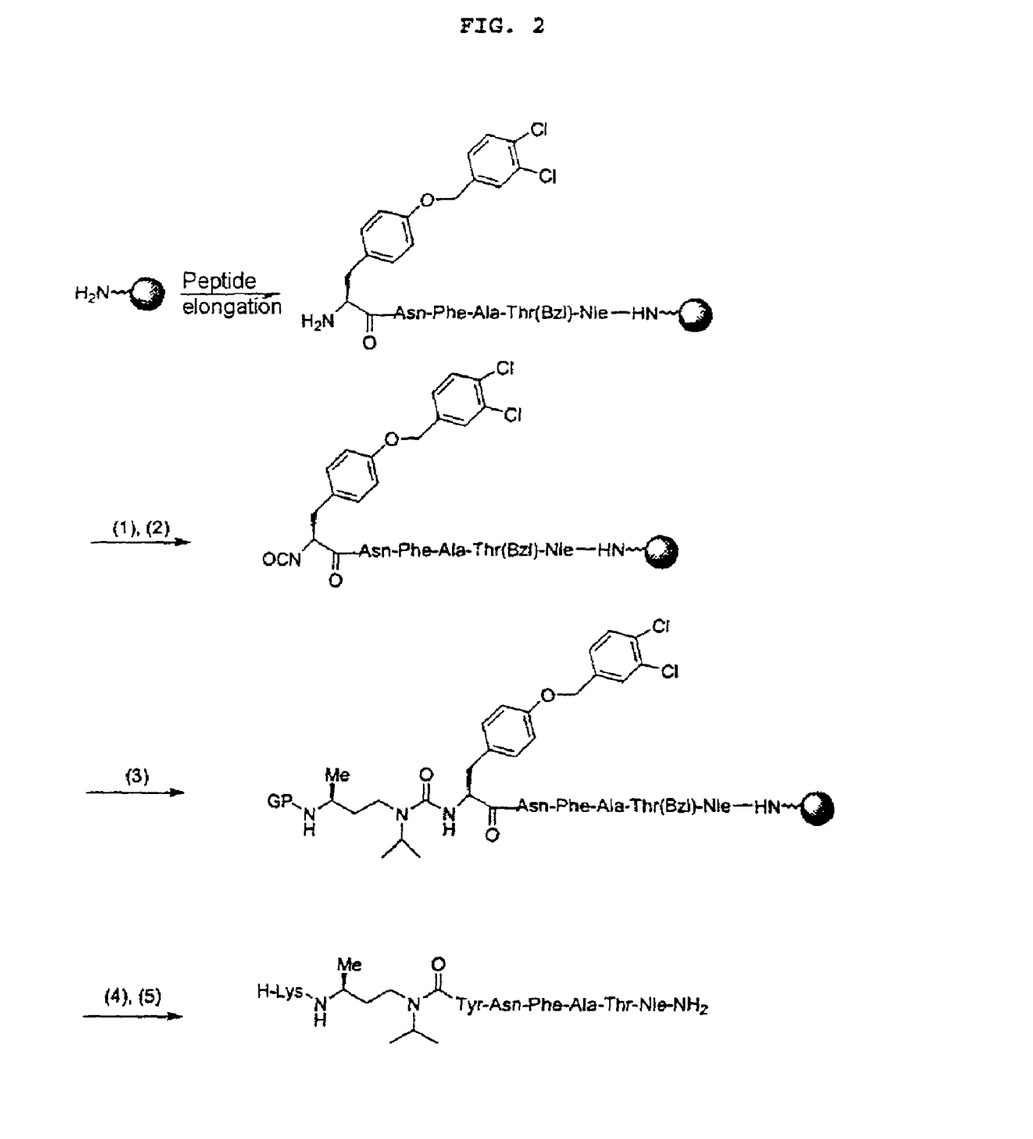
FIG. 2 illustrates the introduction, onto a solid support, of the amine monoprotected via carbonylation, leading to the isocyanate.

Synthesis of a Pseudopeptide Comprising the Carbaza unit B According to Formula I The synthesis of the peptide is carried out as far as the tyrosine residue from an MBHA resin (100 micromoles of resin with a degree of substitution of 0.63 milliequiv./g, reference 400373 from the company Applied Biosystems) on an Applied Biosystems apparatus (model 431) according to conventional methods of peptide synthesis using the Boc or Fmoc strategy for the protection of the amino acids; (see, for example, Synthetic peptides, a user's guide, published by Gregory A. Grant, WH Freeman and Company, New York, 1992 or The Practice of Peptide Synthesis, published by M. Bodanszky and A. Bodanszky, Springer Verlag, Berlin, 1984). The protected diamino molecule 4a or 4b according to the trials is then coupled to an amine via a carbonylating agent according to the scheme described in FIG. 2.

The various steps are described below.

1. 10 equivalents of DIEA relative to the initial grafting of the resin (N,N-diisopropylethylamine, Aldrich, D12,580-6) in 2.5 ml of $CH_2Cl_2$ for 10 min at room temperature.
2. 3.3 equivalents of triphosgene mixed with 10 equivalents of DIEA in 2.5 ml of $CH_2Cl_2$ for 20 min at room temperature. Other conditions according to the carbonylating agent and the protecting group GP are given in the table below.
3. 5 equivalents of compound 4a or 4b in 2.5 ml of $CH_2Cl_2$ for 1 hour at room temperature.
4. Deprotection of GP.
5. Peptide elongation and final cleavage.

Tyr represents tyrosine, Asn asparagine, Phe phenylalanine, Ala alanine, Thr threonine and Nle norleucine.

The final cleavage with simultaneous deprotection is carried out by mixing strong acids according to the procedure described by Fujii et al. (Fujii, N.; Otaka, A.; Ikemura, O.; Akaji, K.; Funakoshi, S.; Hayashi, Y.; Kuroda Y.; Yajima, H. 1987 J. Chem. Soc. Chem. Commun. 274–275) or with hydrofluoric acid in the case of a synthesis with Boc strategy. With Fmoc strategy, the cleavage is carried out with the K reagent (King, D.; Fileds, C.; Fileds, G. 1990 Int. J. Pept. Protein Res. 36, 255–266). The G. 1990 Into. J. Pept. Protein Res. 36, 255–256). [sic] The cleavage of GP is carried out according to the customary methods in peptide synthesis.

After purification by reversed phase preparative HPLC, the pseudopeptide obtained was characterized by analytical HPLC and mass spectrometry as described in the Limal et al. publication (Limal, D.; Briand, J. P.; Dalbon, P.; Jolivet, M.; 1998, J. Peptide Res. 52, 121–129).

The table below shows the various possibilities of synthesis as well as the coupling yields obtained:

TABLE

| Synthesis strategy: nature of GP | Carbonylating reagent Step (2) | Reaction time for the diamine (hour) | Total yield of synthesis of the pseudopeptide after HPLC purification (%) |
|---|---|---|---|
| Boc | Carbo-diimidazole | 1 | 6 |
| Boc | Carbo-diimidazole | 12 | 30 |
| Boc | Carbo-diimidazole | 72 | 35 |
| Boc | Triphosgene | 1 | 35 |
| Boc | Triphosgene | 12 | 32 |
| Boc | Triphosgene | 1 | 40 |
| Fmoc | Triphosgene | 12 | 25 |

Retention time for the pseudopeptide by HPLC: 11 min 88 sec.

MALDI-TOF MS: m/z 1012.05 ($M+H^+$) in agreement with the theoretical weight.

EXAMPLE 3

Synthesis of a Pseudopeptide Comprising the Carbaza Unit B According to Formula II The key molecule for the synthesis of the pseudopeptide is a monoprotected diamine and it is therefore natural to be able to introduce it into the synthesis through either of its amine functional groups. For that, the end comprising the secondary amine of compound 4a was again protected with an Fmoc group and the protected end deprotected with the Boc group. The molecule obtained was introduced onto a solid support in the same manner as above. The molecule represented below is thus obtained with a mass identical to the preceding pseudopeptide compound but with a different retention time.

Retention time by HPLC: 11 min 55 sec (HPLC conditions described in example 2).

MALDI-TOF MS: m/z 1012.05 ($M+H^+$).

The invention claimed is:

1. A pseudopeptide of at least 6 amino acids comprising at least one unit chosen from the B units of general formulae (I) and/or (II):

in which:

$R_1$, $R_2$ and $R_3$ each independently of one another represent an amino acid side chain and may be identical or different, and X represents an oxygen or sulfur atom, wherein the N-terminal of said unit is attached to the C-terminal of an amino acid or of a unit of said general formulae (I) or (II) and/or the C-terminal of said unit is attached to the N-terminal of an amino acid or of a unit of said general formulae (I) or (II).

2. The pseudopeptide as claimed in claim 1 having a size of at least 9 amino acids.

3. The pseudopeptide as claimed in claim 1, characterized in that X represents an oxygen atom.

4. The pseudopeptide as claimed in claim 1, characterized in that $R_2$ represents a hydrogen atom.

5. A method for synthesizing a pseudopeptide as claimed in claim 1, characterized in that a monoprotected diamine of general formula IIIa or IIIb in which: $R_1$, R and $R_3$ each independently of one another represent an amino acid side chain and may be identical or different, and GP represents a group for protecting the amine functional group, is coupled with an amine in the presence of a carbonylating agent.

6. The method as claimed in claim 5, characterized in that GP is a Boc, Fmoc, Cbz or Alloc group.

7. The method as claimed in claim 5, characterized in that the carbonylating agent is chosen from N,N'-carbonyldiimidazole and triphosgene.

8. A reagent for detecting a pathological condition associated with the presence of endogenous or exogenous proteins, characterized in that it comprises, as reactive substance, at least one pseudopeptide as claimed in claim 1.

9. The reagent as claimed in claim 8, characterized in that the pseudopeptide is labeled with a tracer or biotin.

10. The reagent as claimed in clam 8, characterized in that the size of the pseudopeptide is at least 12 amino acids.

11. A kit for detecting a pathological condition associated with the presence of endogenous or exogenous proteins, characterized in that a reagent according to claim 8, is attached to a solid support which is immunologically compatible with said reagent.

12. A method for detecting and/or assaying an antigen present in a sample by a competition technique in which said sample is brought into contact, simultaneously or in two stages, with a predetermined quantity of an antibody directed against a portion of the antigen and a predetermined quantity of a reagent as claimed in claim 8, and the presence and/or the quantity of antigen present in said sample is determined.

13. A method for detecting and/or assaying an antibody present in a sample by a competition technique in which said sample is brought into contact simultaneously with a predetermined quantity of an antigen at least a portion of which is recognized by said antibody and a predetermined quantity of a reagent as claimed in claim 8, and the presence and/or the quantity of antibody present in said sample is determined.

14. A pharmaceutical composition comprising, as active ingredient, at least one pseudopeptide as claimed in claim 1, and a pharmaceutically acceptable excipient.

* * * * *